United States Patent [19]

Kehry et al.

[11] Patent Number: 6,143,507
[45] Date of Patent: Nov. 7, 2000

[54] HIGH THROUGHPUT COMPATIBLE ASSAY FOR RECEPTOR-TRAF INTERACTIONS

[75] Inventors: Marilyn R. Kehry; Steven S. Pullen; James J. Crute, all of Danbury, Conn.

[73] Assignee: Boehringer Ingelheim Pharmaceuticals, Inc., Ridgefield, Conn.

[21] Appl. No.: 09/181,958

[22] Filed: Oct. 29, 1998

[51] Int. Cl.$^7$ .................... G01N 33/53; G01N 33/537; G01N 33/534; C12Q 1/00; C07K 1/00

[52] U.S. Cl. .................... 435/7.1; 435/289.1; 435/305.1; 435/4; 435/7.5; 435/7.92; 435/7.93; 435/7.94; 435/7.95; 435/7.2; 436/501; 436/512; 436/517; 436/518; 436/532; 436/543; 436/544; 436/545; 436/546; 436/804; 436/809; 436/823; 530/350; 530/828; 530/866

[58] Field of Search .................... 435/289.1, 305.1, 435/4, 7.1, 7.5, 7.92–7.95, 7.2; 436/501, 512, 517, 518, 532, 543, 544, 545, 546, 804, 809, 823; 530/350, 828, 866

[56] References Cited

U.S. PATENT DOCUMENTS

| | | | |
|---|---|---|---|
| 4,535,057 | 8/1985 | Dreesman et al. | 435/5 |
| 5,212,063 | 5/1993 | Ofenloch-Hahnle et al. | 435/7.5 |
| 5,670,319 | 9/1997 | Goeddel et al. | 435/6 |
| 5,710,013 | 1/1998 | Goeddel et al. | 435/29 |
| 5,741,667 | 4/1998 | Goeddel et al. | 435/69.1 |
| 5,767,244 | 6/1998 | Goeddel et al. | 530/350 |
| 5,776,702 | 7/1998 | Schmitt et al. | 435/7.5 |
| 5,811,246 | 9/1998 | Anumula et al. | 435/7.5 |
| 5,863,740 | 1/1999 | Kientsch-Engel et al. | 435/7.5 |
| 5,869,275 | 2/1999 | Huang | 435/15 |
| 5,932,433 | 8/1999 | Schatz | 435/15 |

OTHER PUBLICATIONS

Cao Z. et al. TRAF6 is a Signal Transducer for Interleukin–1. Nature 383: pp. 443–446, (1996), Oct. 3, 1996.

Cheng et al. Involvement of CRAF1, a Relative of TRAF, in CD40 Signaling. Science 267: pp. 1494–1498, (1995), Mar. 10, 1995.

Rothe et al. A Novel Family of Putative Signal Transducers Associated with the Crytoplasmic Domain of the 75 kDa Tumor Necrosis Factor Receptor. Cell 78: pp. 681–692, (1994), Aug. 26, 1994.

Hu H. M. et al. A Novel Ring Finger Protein Interacts with the Cytoplasmic Domain of CD40. J. Biol. Chem. 269: pp. 30069–30072, (1994), Dec. 2, 1994.

Regnier et al. Presence of a New Conserved Domain in CART1, a Novel Member of the Tumor Necrosis Factor Receptor–Associated Protein Family, Which Is Expressed in Breast Carcinoma. J. Biol. Chem. 270: pp. 25715–27521, (1995), Oct. 27, 1995.

Nakano et al. TRAF5, an Activator of NF–Alpha B and Putative Signal Transducer for the Lymphotoxin–Beta Receptor. J. Biol. Chem. 271: pp. 14661–14664 (1996), Jun. 21, 1996.

Ishida et al. TRAF5, A Novel Tumor Necrosis Factor Receptor–Associated Factor Family Protein, Mediates CD40 Signaling. Proc. Nalt. Acad. Sci. USA 93: pp. 9437–9442, (1996), Sep. 1996.

Lee et al. CD30/TNF Receptor–Associated Factor Interaction: NF–Alpha B Activation and Binding Specificity. Proc. Nalt. Acad. Sci. USA 93: pp. 9699–9703, (1996), Sep. 1996.

Gedrich et al. CD30 Contains Two Binding Sites with Different Specificities for Members of the Tumor Necrosis Factor Receptor–Associated Factor Family of Singal Transducing Proteins. J. Bio. Chem. 272: pp. 12852–12858, (1996), May 31, 1996.

Marsters et al. Herpesvirus Entry Mediator, A Member of the Tumor Necrosis Factor Receptor (TNFR) Family, Interacts with Members of the TNFR–Associated Factor Family and Activates the Transcription Factors NF–alpha B and AP–1. J. Biol. Chem. 272: pp. 14029, May 30, 1997.

Aizawa et al. TUmor Necrosis Factor Receptor Associated Factor (TRAF) 5 and TRAF2 Are Involved in CD30–Mediated NF alpha B Activation. J. Biol. Chem. 272: pp. 2042–2045, (1997), Jan. 24, 1997.

Arch et al. 4–1BB and Ox40 Are Members of a Tumor Necrosis Factor (TNF)–Nerve Growth Factor Receptor Subfamily that bind TNF Receptor Associated Factors and Activate Nuclear Factor alpha B. Molec. Cell Biol.: 18 pp: 558–565, (1998), Jan. 1998.

Devergne et al. Associatiion of TRAF!1, TRAF2, and TRAF3 with an Epstein–Barr Virus LMP1 Domain Important for B–Lymphocyte Transformation: Role in NF–alpha B Activation, Molec. Cell Biol. 16: pp. 7088–7108, (1996), Dec. 1996.

Mike Rothe, et al; TRAF2–Mediated Activation of NF–κB by TNF Receptor 2 and CD40, Science, vol. 269, Sep. 8, 1995, pp 1424–1427.

Louis–Martin Boucher, et al; Binding Sites of Cytoplasmic Effectors TRAF1, 2, and 3 on CD30 and Other Members of the TNF Receptor Superfamily, Biochemical and Biophysical Research Communications 233, 592–600 (1997), Article RC976509.

George Mosialos, et al; The Epstein–Barr Virus Transforming Protein LMP1 Engages Signaling Proteins for the Tumor Necrosis Factor Receptor Family, Cell, vol. 80, 389–399, Feb. 10, 1995.

*Primary Examiner*—Christopher L. Chin
*Assistant Examiner*—Pensee T. Do
*Attorney, Agent, or Firm*—Robert P. Raymond; Anthony P. Bottino; Alan R. Stempel

[57] ABSTRACT

Disclosed is a high throughput compatible assay that is useful for the identification of specific antagonists of TRAF-receptor interactions. The modular flexibility of the assay makes it possible to introduce simple modifications in order to measure the interaction of any TNF receptor cytoplasmic domain (or TRAF-binding protein) with any of the six TRAF proteins, TRAF1, TRAF2, TRAF3, TRAF4, TRAF5 and TRAF6.

7 Claims, 2 Drawing Sheets

HIGH THROUGHPUT COMPATIBLE ASSAY FOR RECEPTOR-TRAF INTERACTIONS

BACKGROUND OF THE INVENTION

1. Field of the Invention

The invention relates to screening assays for compounds effecting TRAF-receptor interactions and is useful for the identification of agonists and antagonists of TRAF-receptor interactions.

2. Description of Related Art

Tumor necrosis factor (TNF) receptor superfamily members regulate cellular proliferation, differentiation, and apoptosis in inflammatory and immune responses. Signaling through TNF receptor superfamily members is initiated by oligomerization of the receptors with trimeric ligands bringing intracellular domains in close proximity. Signal transduction through many of these receptors is mediated in part by a recently identified family of proteins termed TNF receptor-associated factors (TRAFs). Six TRAF family members have been identified. Cao, Z., et al (1996) *Nature* 383, 443–446; Cheng, G. et al 995 *Science* 267, 1494–1498; Rothe, M., et al (1994) *Cell* 78, 681–692; Sato, T., et al (1995) *FEBS Letters* 358, 113–118; Hu, H. M., et al (1994) *J. Biol. Chem.* 269, 30069–30072; Mosialos, G., et al (1995) *Cell* 80, 389–399; Regnier, C. H., et al (1995)*J. Biol. Chem.* 270,25715–25721; Nakano, H., et al (1996) *J. Biol. Chem.* 271, 14661–14664. Subsets of TRAF proteins have been shown to interact with the TNF receptor family members TNFR2, CD40, CD30, LTBR, ATAR, OX-40, and 4-1BB. Cheng et al (1995); Rothe et al (1994); Sato et al (1995); Hu et al (1994); Nakano et al (1996); Ishida, T. K., et al (1996) *Proc. Natl. Acad. Sci. U. S. A.* 93, 9437–9442; Ishida, T., et al (1996) *J. Biol. Chem.* 271, 28745–28748; Boucher, L. M., et al (1997) *Biochem. Biophys. Res. Commun.* 233, 592–600; Lee, S. Y., et al (1996) *Proc. Natl. Acad. Sci. U. S. A.* 93, 9699–9703; Gedrich, R. W., et al (1996) *J. Biol. Chem.* 271, 12852–12858; Marsters, S. A., et al (1997) *J. Biol. Chem.* 272, 14029–14032; Aizawa, S. et al (1997) *J. Biol. Chem.* 272, 2042–2045; Arch, R. H. et al (1998) *Molec. Cell Biol.* 18, 558–565; Devergne, O., et al (1996) *Molec. Cell Biol.* 16, 7098–7108; VanArsdale, T. L., et al (1997) *Proc. Natl. Acad. Sci. U.S.A.* 94, 2460–2465. The conserved C-terminal region of TRAFs (TRAF(NC), also delineated the TRAF domain) binds to receptor cytoplasmic domains. Cheng et al (1995); Takeuchi, M., et al (1996)*J. Biol. Chem.* 271, 19935–19942; Rothe, M., et al (1995) *Science* 269, 1424–1427. The initial event in signaling is thought to be mediated by a transient recruitment of TRAF proteins following receptor cross-linking. Kuhne, M. R., et al (1997)*J. Exp. Med.* 186, 337–342. The interaction of TRAF proteins with cross-linked receptor cytoplasmic domains is therefore a critical step in TNF receptor family member signaling and determines the specificity of the resulting cellular response.

Thus, it is apparent that there is a clear need for a quantitative binding assay for TRAF-receptor interactions and which has the modular flexibility to make possible the introduction of simple modifications in order to measure the interaction of any TNF receptor cytoplasmic domain (or TRAF-binding protein) with any of the six TRAF proteins. Such an assay would be useful for identification of specific agonists or antagonists of these interactions.

SUMMARY OF THE INVENTION

All of the above factors provide a strong incentive for the development of an efficient, accurate and reproducible assay capable of quantifying TRAF and TRAF interacting receptor binding. The assays of the present invention are useful in pharmacological studies of these interactions and provide an efficient alternative to the use of receptor—TRAF co-precipitation assays or yeast two hybrid interaction assays. It is therefore an object of the present invention to provide a quantitative assay for measuring the ability of a substance to effect binding of a TRAF protein to a TRAF interacting receptor, the assay performed by providing the receptor having a cytosolic binding domain or fragment thereof, wherein the receptor is bound to a multi-well plate, the multi-well plate being capable of allowing formation of a multimeric receptor and being capable of allowing detection of a signal; providing a TRAF protein or fragment thereof possessing a terminal tag, the tag having one or more amino acids and being capable of binding a signal-generating antibody or fragment thereof; providing the substance; combining the receptor bound to the well, the TRAF protein and the substance; and detecting the signal-generating antibody.

In certain specific embodiments, there are provided quantitative assays according to the invention with specific TRAF proteins and their respective receptors, and a multi-well plate having a scintillant and a signal-generating antibody which has a radioactive isotope.

DETAILED DESCRIPTION OF THE INVENTION

Figure 1:
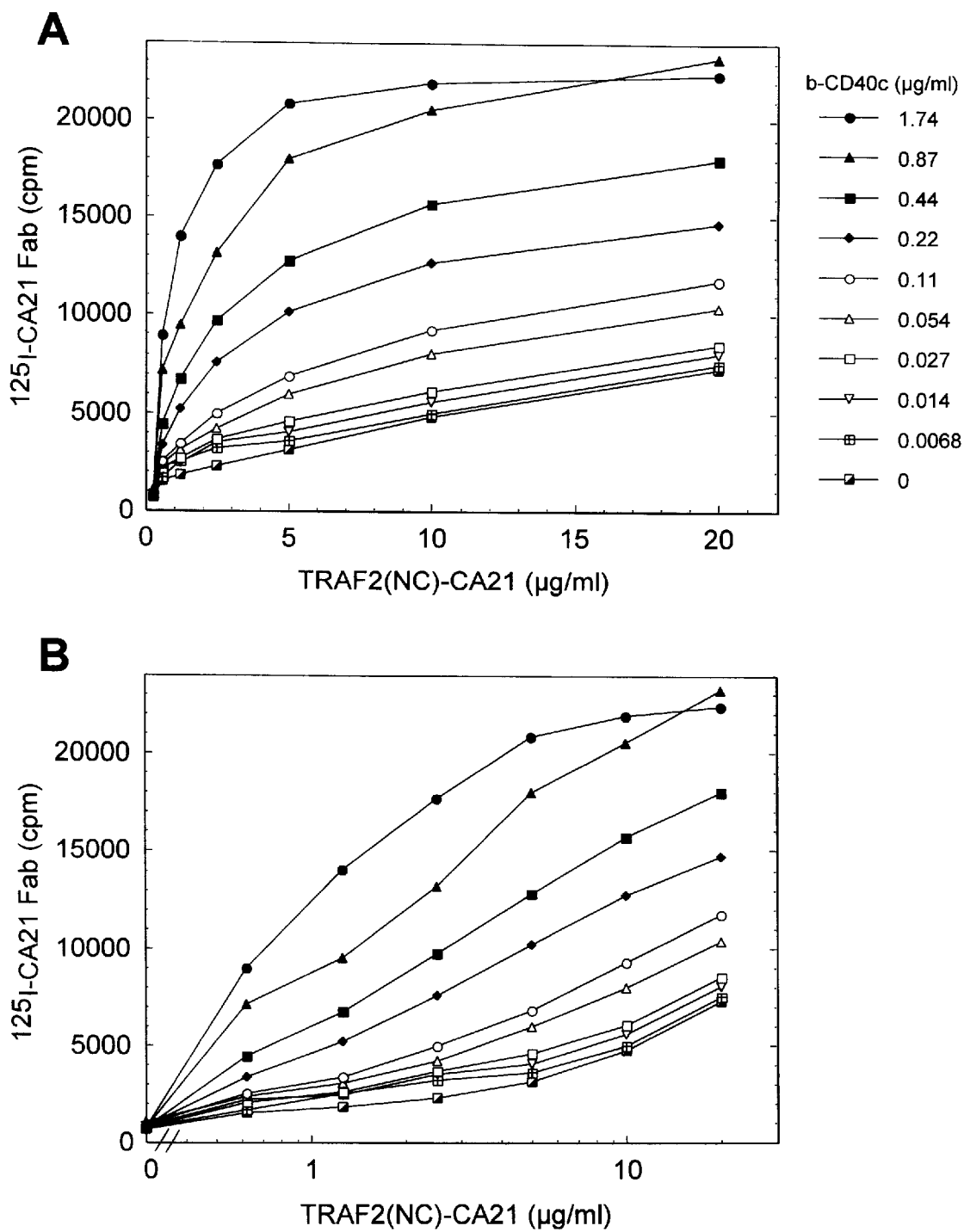
FIG. 1. Two-way titration of biotin-CD40c and TRAF2 (NC)-CA21. Streptavdin flashplates were coated with serial dilutions of biotin-CD40c, starting at 1.74 μg/ml. Purified TRAF2(NC)-CA21 was serially diluted starting at 20 μg/ml. Detection was with $^{125}$I-CA21 Fab (0.08 μCi/well). Background was not subtracted and is listed as biotin-CD40c at 0 μg/ml. Biotin-CD40c concentrations are indicated. A) linear plot; B) log plot of TRAF2(NC)-CA21 concentration for the same experiment in A).

The assay according to the invention, is a high throughput compatible assay that is useful for the identification of specific antagonists of TRAF-receptor interactions. The modular flexibility of the assay makes it possible to introduce simple modifications in order to measure the interaction of any TNF receptor cytoplasmic domain (or TRAF-binding protein) with any of the six TRAF proteins, TRAF1, TRAF2, TRAF3, TRAF4, TRAF5 and TRAF6.

The multi-well plate according to the invention is any multi-well plate capable of allowing detection of a signal. For example, in a preferred embodiment, a flashplate design was chosen for the assay. In a flashplate design, a scintillant-embedded 96-well plate precoated with a substance capable of multimerizing the receptor such as streptavidin.

The assay according to the invention can use a TRAF interacting receptor such as ATAR, LT-BR, TNFR2, CD40, CD30, OX-40 and 4-1BB, preferably CD40. The 62 amino acid CD40 cytoplasmic domain (CD40c) was expressed in *E. coli* and purified as described in Example 2 below. Analytical ultracentrifugation studies showed that the CD40c protein was a monomer. CD40c had a weak ability to compete for GST-CD40-TRAF interaction. Pullen, S. S., et al (1998) *Biochem.*, 37 11836–11845. When coated on standard 96-well plates and used to bind TRAF molecules the CD40c gave a weaker signal than dimeric GST-CD40. Therefore, to design the CD40c-TRAF interaction assay, CD40c was conjugated with biotin. Streptavidin-coated wells were used to multimerize CD40c, each streptavidin tetramer being capable of binding a maximum of four biotin-CD40c molecules. This approach was predicted to mimic the results of receptor cross-linking by trimeric ligands.

To establish a uniform signal for TRAF binding that would not be amplified during detection by artificial (antibody-induced) cross-linking, defined and purified protein components are preferred. Because of the difficulty in purifying recombinant full-length TRAF, the present invention utilizes TRAF(NC) domains, preferably of TRAF2 and TRAF3, possessing a C-terminal tag with a nine amino acid epitope that is recognized by the CA21 monoclonal antibody. Kahn, J., et al (1994) *J. Cell Biol.* 125, 461–470. The TRAF2(NC)-CA21 and TRAF3(NC)-CA21 proteins as shown in sequence nos. 1 and 2, respectively, were expressed in insect cells and purified by ion exchange chromatography and hydroxyapatite chromatography as described herein. Chemical cross-linking, analytical ultracentrifugation and laser light scattering methods demonstrated that the TRAF(NC) domains of TRAF2 and TRAF3 formed homogeneous noncovalent trimers.

Detection of the bound TRAF(NC) proteins is performed with a signal-generating antibody. A signal-generating antibody is any antibody or fragment thereof possessing specificity for the tag as described herein. The signal-generating antibody is also capable of generating a signal by means known in the art, for example, by possessing a fluorophore or radiolabel. In a preferred embodiment, the signal-generating antibody is a Fab fragment of the CA21 monoclonal antibody. The CA21 Fab can be radiolabeled with, for example, radioactive iodine as described herein, and the specific activity adjusted continuously for radioactive decay according to the half life of the radiolabel. Radioactivity bound to the scintillant-embedded wells indicated TRAF binding and could be detected with minimal background by scintillation counting the plates without removal of the radioactive solution.

To establish and optimize the assay parameters for the detection of signaling inhibitors it was desired to obtain a suboptimal signal while retaining a good signal/noise ratio. Additionally, it was desired to minimize the quantity of TRAF interacting receptor and obtain a good dynamic range of signal. In this design, inhibitors of CD40-TRAF interaction as well as enhancers/stabilizers of the interaction could be readily detected. Since CD40-TRAF interaction is thought to be transient (Kuhne et al (1997)), both inhibitors and enhancers of the interaction would be expected to antagonize cellular signaling.

Figure 2:
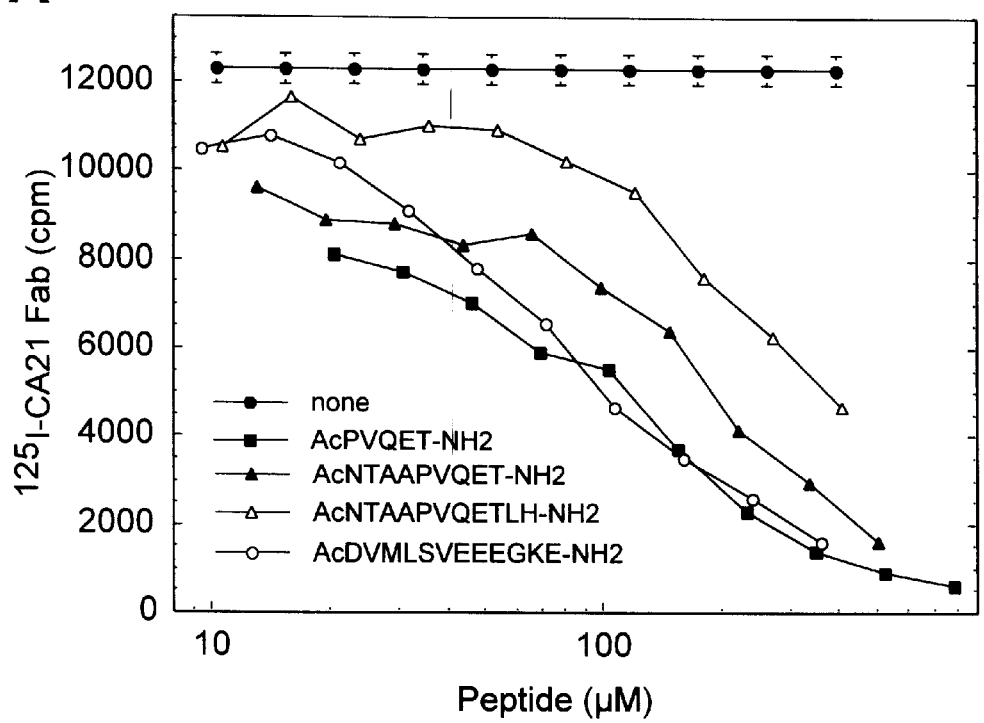
FIG. 2. Peptide antagonists of CD40c-TRAF2 interaction. Streptavidin flashplates were coated with 0.44 μg/ml biotin-CD40c. Stock solutions of peptides were prepared at 1 mg/ml in assay buffer and the pH verified. All peptides were assayed by preincubating with TRAF2(NC)-CA21 at a final peptide concentration of 0.5 mg/ml. Peptides were serially diluted 1.5-fold prior to addition of the TRAF2(NC)-CA21 (5 μg/ml final). Results are means of duplicate points except for the no inhibitor wells (none, closed circles) that are means i standard deviation of 11 replicates. A) Peptides AcPVQET-NH2 (closed squares), AcNTAAPVQET-NH2 (closed triangles), AcNTAAPVQETLH-NH2 (open triangles), CD30.B (AcDVMLSVEEEGKE-NH2, open circles); B) Peptides AcIQET-NH2 (closed squares), AcPIQET-NH2 (closed triangles), AcQEPQEINF-NH2 (open triangles), CD40c (open circles). The maximum signal in B) is less due to a difference in the decay of the $^{125}$I-Fab.
Figure 2:
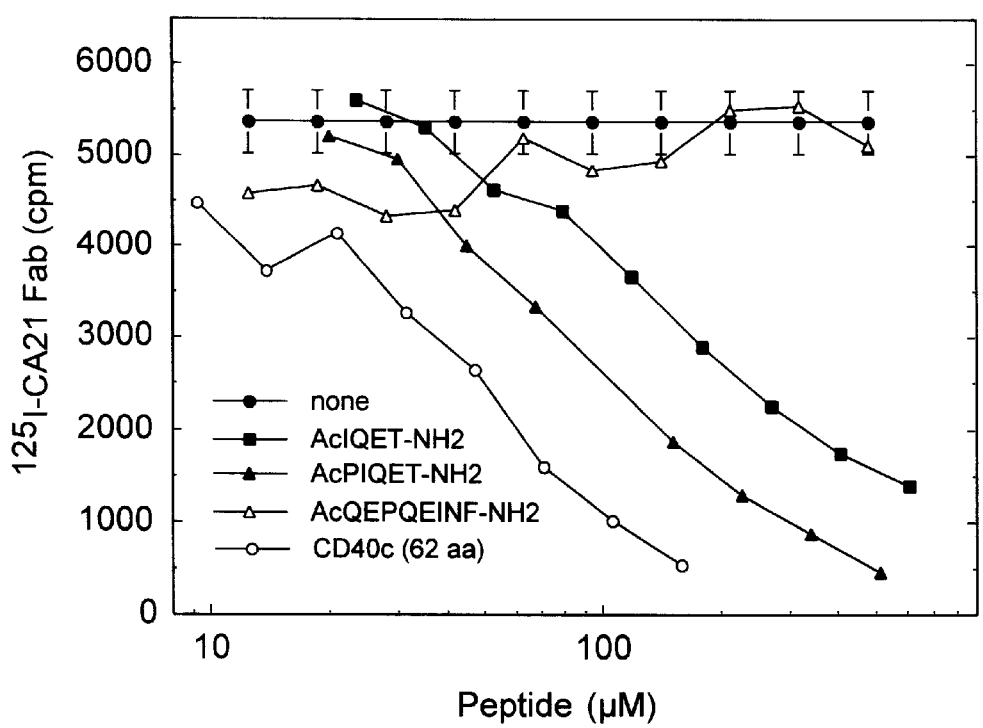

The assay parameters were established with a two-way titration of biotin-CD40c and TRAF2(NC)-CA21, as shown in FIG. 1. The assay showed saturation with increasing concentrations of TRAF2(NC)-CA21, and gave a good dose response for biotin-CD40c. Maximal signal was obtained with approximately 2 μg/ml biotin-CD40c, and the signal did not increase further up to 20 μg/ml. Significant signal was detectable as low as 0.054 μg/ml biotin-CD40c (FIG. 1). Standard conditions for the assay were selected to be 0.44 μg/ml CD40c and 5 μg/ml TRAF2(NC)-CA21. These conditions provided a signal/noise of eight to ten and a good dynamic range for the detection of inhibitors or enhancers. DMSO at concentrations up to 10% (v/v) did not inhibit the assay. As noted by the manufacturer of the plates, low concentrations of detergents were strong inhibitors of the assay because they removed the streptavidin from the wells. To demonstrate the use and specificity of the assay several N-terminally acetylated and C-terminally amidated peptides derived from the cytoplasmic domains of CD40 and CD30 were assayed for the ability to inhibit CD40c-TRAF2 interaction. The PVQET sequence in the CD40 cytoplasmic domain is essential for signaling through CD40 and is thought to be a core TRAF2 binding sequence. Devergne, O., et al (1996) *Mol. Cell. Biol.* 16, 7098–7108; Innui, W., et al (1990) *Eur. J Immunol.* 20, 1747–1753. Therefore several peptides around the PVQET sequence were tested for the ability to compete the CD40c-TRAF2 interaction (FIG. 2A). Three different peptides containing the PVQET sequence were found to inhibit CD40c-TRAF2 binding. The longest peptide, an 11-mer, was the least potent, and the shortest peptide, PVQET, was the most potent, with an $IC_{50}$ of approximately 90 μM. The activity of PVQET was comparable to a 12 amino acid residue TRAF2-binding peptide derived from the CD30 cytoplasmic domain (Boucher et al (1997)). FIG. 2A. The nonbiotinylated CD40c polypeptide had an $IC_{50}$ of approximately 50 μM. A CD40-derived peptide non-overlapping with the PVQET peptide that has been demonstrated to bind TRAF6 (26) did not inhibit CD40c-TRAF2 interaction (FIG. 2B). Alteration of the PVQET sequence to PIQET resulted in a slightly increased inhibitory activity ($IC_{50}$~70 μM), as predicted by amino acid replacement analyses on the TRAF2 binding peptide derived from CD40. Additionally, removal of the $^{250}$Pro residue to produce a four amino acid residue peptide, IQET, resulted in a approximately two-fold decrease of inhibitory activity ($IC_{50}$~140 μM) (FIG. 2B).

Similar assay results have also been obtained with the same peptide competitors using 5 μg/ml TRAF3(NC)-CA21 instead of TRAF2(NC)-CA21. Thus, it would be expected that either TRAF1(NC)-CA21 or TRAF6(NC)-CA21 could be also substituted for TRAF2 in binding to biotin-CD40c. Pullen et al (1998). Alternatively, biotin-conjugated cytoplasmic domains of other TRAF-interacting receptors such as ATAR/HVEM or LT-R could be substituted for biotin-CD40c. The alternative of using a $^3$H-Fab fragment is also a possibility that would decrease the need for frequent radio-iodinations. These variations on the assay show its adaptability and utility as a specificity assay. For example, in a set of assays measuring CD40c-TRAF2, CD40c-TRAF3, ATARc-TRAF2, or ATARc-TRAF3 interaction, it could readily be determined whether an inhibitor targeted CD40c, ATARc, TRAF2, or TRAF3, or was nonspecific.

As will be appreciated by those skilled in the art, the assay can be used to derive peptide-based as well as non-peptide small molecule antagonists of TRAF-mediated signaling. Targets would include receptor cytoplasmic domains or individual TRAF proteins.

In order that this invention be more fully understood, the following examples are set forth. These examples are for the purpose of illustrating preferred embodiments of this invention, and are not to be construed as limiting the scope of the invention in any way.

All references cited in this application are fully incorporated by reference.

EXAMPLE 1

Plasmids and viruses

The human CD40 cytoplasmic domain, amino acids 216–277, was PCR amplified using oligonucleotides 5'-CCGGGCCATGGCCAAAAAGGTGGCCAA GAAGCCAACC-3' and 5'-CCCGGGAATTCTCATCACTGTCTCTCC TGCACTGAGATGCG-3' and ligated into pCR2.1 (In Vitrogen) to generate pCD40c. The NcoI to EcoRI fragment was ligated into pET-23d to generate pCD40c/pET23d.

Full-length human TRAF2 and TRAF3 were PCR amplified from a PHA-stimulated human peripheral blood leukocyte cDNA library (Clontech) using oligonucleotides 5'-AAAAGGAAAAGCGGCCGCTTATTAGAGCCC TGTCAGGTCCA-3' and 5'-TTGGTTGGATCCTATAAATATGGCTGCAGC TAGCGTGA-3' for TRAF2 and oligonucleotides 5'-TTGGTTGGATCCTATAAATATGGAGTCGAG TAAAAAGATGGACTC-3' and 5'-GCGGCCGCTCATCAGGGATCGGGCAGATCCGA-3' for TRAF3, and ligated into pGem-T (Promega) to make pTRAF2/GemT and pTRAF3/GemT, respectively. The TRAF2(NC) domain (amino acids 272–501) and TRAF3 (NC) domain (amino acids 354–568) were PCR amplified from pTRAF2/GemT and pTRAF3/GemT, respectively, using oligonucleotides 5'-CCATGGCCTGCGAGAGCCTGGAGAAGAAGA CGGCCACTTTTGA-3' and 5'-AAAAGGAAAAGCGGCCGCTTATTAGAG CCCTGTCAGGTCCA-3' for TRAF2(NC) and oligonucleotides 5'-CCATGGTGGAGTCCCTCCAGAACCGCG TGACCGAGCT-3' and 5'-GCGGCCGCTCATCAGGGATCGGGCAGATCCGA-3' for TRAF3(NC) respectively, and ligated into pGem-T to create pTRAF2(NC)/GemT and pTRAF3(NC)/GemT, respectively. An NcoI linker (CCCATGGG) (New England Biolabs) was ligated into the transplacement vector pVL1 393 (In Vitrogen) after digestion with SmaI to create pVL1393/NcoI+. The NcoI to NotI TRAF(NC) domain-containing fragments from pTRAF2(NC)/GemT and pTRAF3(NC)/GemT were ligated into pVL1 393/NcoI+ to create pTRAF2(NC)/1393 and pTRAF3(NC)/1393, respectively. The TRAF(NC) domain constructs of TRAF2 and TRAF3 were C-terminally tagged with the nine amino acid epitope (SKRSMNDPY) recognized by the CA21 monoclonal antibody (Kahn et al (1994)) by PCR methods to generate TRAF2(NC)-CA21 and TRAF3(NC)-CA21 in pVL1393. Recombinant baculovirus stocks were generated by standard methods from the transplacement vectors described above. O'Reilly, D. R., Miller, L. K., and Luckow, V. A. (1992) Baculovirus expression vectors: a laboratory manual., W. H. Freeman & Co., Salt Lake City, Utah.

EXAMPLE 2

Protein expression and purification

Spodoptera frugiperda (Sf21) cells were maintained and infected by standard procedures (O'Reilly et al (1992); Dracheva, S., et al (1995) J. Biol. Chem. 270, 14148–14153) using medium supplemented with 5% heat-inactivated fetal bovine serum (Hyclone) and 50 µg/ml gentamicin sulfate (Life Technologies, Inc.). All purification procedures were performed at 4° C. Cytosolic extracts of TRAF(NC)-CA21 baculovirus-infected Sf21 cells were prepared as described (Dracheva et al (1995)), without the addition of ATP or $MgCl_2$, frozen under liquid nitrogen, and stored at −80° C. Saturated ammonium sulfate was added to 43% v/v with mixing and incubated at 0° C. for 2 hr. Precipitated proteins were harvested by centrifugation, and the pellet was resuspended in buffer A (20 mM HEPES, pH 7.0, 200 mM NaCl, 1 mM DTT, 10% v/v glycerol, 0.1 mM EDTA, 0.1 mM EGTA, and 1 mM PMSF) with 200 mM NaCl. The NaCl concentration was adjusted to 100 mM by dilution with buffer A, and the sample was applied to coupled Source 15S and Source 15Q columns (Amersham Pharmacia Biotech) equilibrated in buffer A with 80 mM NaCl. The material flowing through both columns was collected and applied to a Ceramic Hydroxyapatite (Type II) column (BioRad) equilibrated in buffer B (50 mM potassium phosphate pH 6.2, 100 mM NaCl, 0.2 mM DTT. 1 mM PMSF). Proteins were eluted with a 0 to 55% gradient of buffer C (500 mM potassium phosphate pH 6.2, 0.2 mM DTT). Peak fractions were pooled and purified proteins were quantitated as described (Gill, S. C., and von Hippel, P. H. (1989) Anal. Biochem. 182, 319–326), frozen in aliquots under liquid nitrogen, and stored at −80° C. Expression of CD40c in Escherichia coli strain BL21 (DE3) was by induction with 1.0 mM IPTG for 3 h at 37° C. Harvested cell paste was resuspended in 2 volumes of lysis buffer (20 mM HEPES, pH 7.5, 200 mM NaCl, 1 mM DTT, 1 mM EDTA, 1 mM EGTA, 1 0% v/v glycerol, 1 mM PMSF, 4 µg/ml leupeptin, 4 µg/ml pepstatin A), frozen under liquid nitrogen, and stored at −80° C. Thawed cell paste was resuspended in an equal volume of lysis buffer, and cells were disrupted by nitrogen cavitation. Extracts were clarified by ultracentrifugation for 75 min at 100,000×g. Saturated ammonium sulfate was added to 66% v/v with mixing and incubated at 0° C. for 2 hr. Precipitated proteins were harvested by centrifugation, and the pellet was resuspended in buffer A with 200 mM NaCl. After dialysis overnight in buffer A with 100 mM NaCl, the sample was applied to a Source 15S column (Amersham Pharmacia Biotech) equilibrated in buffer A in 80 mM NaCl. Proteins were eluted with a 5 to 55% gradient of buffer A with 2 M NaCl. Peak fractions were pooled and purified protein was quantitated using a Micro BCA assay (Pierce Chemical Co.) relative to GST-CD40c (26) as a standard, frozen in aliquots under liquid nitrogen, and stored at −80° C.

Purified CD40c (1.1 mg/ml) was conjugated to biotin in 0.1 M sodium bicarbonate by the addition of D-biotinoyl-aminocaproic acid-N-hydroxysuccinimide ester (Boehringer Mannheim) at a final concentration of 60 µg/ml. Reagent was removed by dialysis against 40 mM HEPES, pH 7.5, 0.1 M NaCl, 1 mM $MgCl_2$, 0.1 mM DTT. Incorporation of biotin was quantitated by mass spectroscopy and was either one or two mol biotin per mol CD40c. Approximately half of the CD40c remained unconjugated. Biotin-CD40c was titrated in the flashplate assay (below) to empirically determine optimal assay concentrations.

EXAMPLE 3

CA21 Cell Line

The CA21 cell line producing a mouse IgG1 monoclonal antibody against a peptide epitope was grown and purified as described. Kahn et al (1994); Dracheva et al (1995).

Specifically, production of CA21 monoclonal antibody is performed as follows: CA21 hybridoma cell lines producing monoclonal antibodies directed against the cytoplasmic domain of L-selectin were prepared by hyperimmunization of BALB/c mice with a synthetic peptide corresponding to the entire cytoplasmic domain of L-selectin, as described in Kishimoto, T. K., (1990) *Proc. Natl. Acad. Sci. USA* 87, 2244–2248, incorporated herein by reference. Spleen cells were fused with the Sp2/O-Ag14 myeloma fusion partner. Reference in this regard can be made to Shulman, M., et al. (1978) *Nature* 276, 269–270; Mandal, C. et al. (1991) *Hybridoma* 10, 459–466; and Norris, S. H., et al. (1991) *J. Pharm. Biomed. Anal.* 9, 211–217, the entire contents of each are herein incorporated by reference. Hybridoma supernatants were screened for the ability to specifically recognize immobilized cytoplasmic domain peptide. Positive clones were further screened for the ability to immunoprecipitate L-selectin. CA21 (IgG1) monoclonal antibody was purified by protein G affinity chromatography.

EXAMPLE 4

Fab Fragments

Fab fragments were prepared by protease digestion by standard methods (Peters, J. H., and Baumgarten, H. (1992) *Monoclonal antibodies*, Springer-Verlag, p. 276) and iodinated by the IODO-GEN® method. Millar, W. T., and Smith J. F. B. (1983) *Int. J. Appl. Radiat. Isot.* 34, 639–641. Radiolabeled Fab fragment was purified by gel filtration on Sephadex G50-50 and stored at 4° C. in 1% BSA (Sigma) in Dulbecco's phosphate buffered saline (D-PBS), pH 7.4 (GIBCO-BRL).

EXAMPLE 5

Flashplate Assay

Biotin-CD40c (0.5 μg/ml) was bound to streptavidin-coated 96-well scintillant-embedded plates (Flashplates, New England Nuclear, catalog #15112) overnight at 4° C. in D-PBS, 0.1 mM DTT, 0.01% BSA (100 μl/well). Plates were blocked for 2 hr at room temperature by the addition of Dulbecco's-PBS, 0.1 mM DTT, 1.0% BSA (100 μl/well). In a separate 96-well round bottom polypropylene plate peptide inhibitors were diluted in 40 mM HEPES, pH 7.5, 0.1 M NaCl, 1.0 mM $MgCl_2$, 0.1 mM DTT, 0.01% BSA, and TRAF2(NC)-CA21 was added at a final concentration of 5 μg/ml. Plates were preincubated for 30 min at room temperature. After washing the biotin-CD40c-coated flashplate three times with D-PBS, 0.1 mM DTT, inhibitor-TRAF2 (NC)-CA21 mixtures were transferred from the preincubation plate to the washed plate (100 μl/well). Alternatively, after washing the biotin-CD40c-coated flashplates, inhibitors were added directly without TRAF preincubation in a final volume of 50 μl 40 mM HEPES, pH 7.5, 0.1 M NaCl, 1.0 mM $MgCl_2$, 0.1 mM DTT, 0.01% BSA, and 50 μl/well TRAF2(NC)-CA21 (10 μg/ml stock to make a final concentration of 5 μg/ml) was added. Flashplates were incubated for 1 hr at room temperature, washed three times with 40 MM HEPES, pH 7.5, 0.1 M NaCl, 1.0 mM $MgCl_2$, 0.1 mM DTT, and 100 μl/well of [$^{125}$I]CA21 Fab fragment at an adjusted specific activity of 0.08 μCi/well added in 40 nM HEPES, pH 25 7.5, 0.1 M NaCl, 1.0 mM $MgCl_2$, 0.1 mM DTT, 0.1% BSA. After a 1 hr incubation at room temperature plates were sealed and counted in a TopCount scintillation counter (Packard; one minute/well, 2 minute plate delay).

EXAMPLE 6

Peptide Inhibitors

Peptides (5 mg each) were purchased from AnaSpec (San Jose, Calif.) and were synthesized N-terminally acetylated and C-terminally amidated. Peptides were purified to >95% purity as judged by quantitative HPLC analysis and mass spectroscopic analysis.

---

We claim:

1. A quantitative assay for measuring the ability of an antagonist or agonist to effect binding of a TRAF protein or fragment thereof to a TRAF interacting receptor having a cytosolic binding domain or fragment thereof, the TRAF protein or fragment thereof comprising SEQ ID NO: 1 residues 1–240 or SEQ ID NO:2 residues 1–225, the assay comprising:

provwellsignal allowingbody fragment receptor a cytosolicbinding domain or fragment thereof, wherein the receptor is bound to a multi-well plate, the multi-well plate allowing formation of a multimeric receptor and allowing detection of a signal; providing the TRAF protein or fragment thereof possessing a terminal tag, the tag comprising one or more amino acids and allowing binding a signal-generating antibody or fragment thereof; providing the antagonist or agonist; combining the receptor bound to the well, the TRAF protein and the antagonist or agonist; detecting the signal-generating antibody and measuring the inhibition or enhancement of the antagonist or agonist.

2. The assay according to claim 1 wherein the TRAF interacting receptor is selected from the group consisting of ATAR, LT-BR, TNFR2, CD40, CD30, OX-40 and 4-1BB.

3. The assay according to claim 1 wherein the TRAF interacting receptor is conjugated with biotin and the multi-plate well is coated with streptavidin.

4. The assay according to claims 2 or 3 wherein the multi-well plate comprises a scintillant and the signal-generating antibody possesses a radioactive isotope.

5. The assay according to claim 4 wherein the TRAF interacting receptor is CD40.

6. The assay according to claim 1 wherein the antagonist or agonist is added directly to the well.

7. The assay according to claim 1 wherein the antagonist or agonist is preincubated with the TRAF protein or fragment thereof.

* * * * *

SEQUENCE LISTING

<160> NUMBER OF SEQ ID NOS: 2

<210> SEQ ID NO 1
<211> LENGTH: 243
<212> TYPE: PRT
<213> ORGANISM: human

<400> SEQUENCE: 1

```
Cys Glu Ser Leu Glu Lys Lys Thr Ala Thr Phe Glu Asn Ile Val Cys
 1               5                  10                  15

Val Leu Asn Arg Glu Val Glu Arg Val Ala Met Thr Ala Glu Ala Cys
            20                  25                  30

Ser Arg Gln His Arg Leu Asp Gln Asp Lys Ile Glu Ala Leu Ser Ser
        35                  40                  45

Lys Val Gln Gln Leu Glu Arg Ser Ile Gly Leu Lys Asp Leu Ala Met
    50                  55                  60

Ala Asp Leu Glu Gln Lys Val Leu Glu Met Glu Ala Ser Thr Tyr Asp
65                  70                  75                  80

Gly Val Phe Ile Trp Lys Ile Ser Asp Phe Ala Arg Lys Arg Gln Glu
                85                  90                  95
```

```
Ala Val Ala Gly Arg Ile Pro Ala Ile Phe Ser Pro Ala Phe Tyr Thr
            100                 105                 110

Ser Arg Tyr Gly Tyr Lys Met Cys Leu Arg Ile Tyr Leu Asn Gly Asp
            115                 120                 125

Gly Thr Gly Arg Gly Thr His Leu Ser Leu Phe Phe Val Val Met Lys
130                 135                 140

Gly Pro Asn Asp Ala Leu Leu Arg Trp Pro Phe Asn Gln Lys Val Thr
145                 150                 155                 160

Leu Met Leu Leu Asp Gln Asn Asn Arg Glu His Val Ile Asp Ala Phe
                165                 170                 175

Arg Pro Asp Val Thr Ser Ser Phe Gln Arg Pro Val Asn Asp Met
                180                 185                 190

Asn Ile Ala Ser Gly Cys Pro Leu Phe Cys Pro Val Ser Lys Met Glu
            195                 200                 205

Ala Lys Asn Ser Tyr Val Arg Asp Asp Ala Ile Phe Ile Lys Ala Ile
            210                 215                 220

Val Asp Leu Thr Gly Leu Ala Ser Ala Ser Ser Lys Arg Ser Met Asn
225                 230                 235                 240

Asp Pro Tyr

<210> SEQ ID NO 2
<211> LENGTH: 228
<212> TYPE: PRT
<213> ORGANISM: human

<400> SEQUENCE: 2

Val Glu Ser Leu Gln Asn Arg Val Thr Glu Leu Glu Ser Val Asp Lys
  1               5                  10                  15

Ser Ala Gly Gln Val Ala Arg Asn Thr Gly Leu Leu Glu Ser Gln Leu
            20                  25                  30

Ser Arg His Asp Gln Met Leu Ser Val His Asp Ile Arg Leu Ala Asp
            35                  40                  45

Met Asp Leu Arg Phe Gln Val Leu Glu Thr Ala Ser Tyr Asn Gly Val
        50                  55                  60

Leu Ile Trp Lys Ile Arg Asp Tyr Lys Arg Arg Lys Gln Glu Ala Val
 65                  70                  75                  80

Met Gly Lys Thr Leu Ser Leu Tyr Ser Gln Pro Phe Tyr Thr Gly Tyr
                85                  90                  95

Phe Gly Tyr Lys Met Cys Ala Arg Val Tyr Leu Asn Gly Asp Gly Met
            100                 105                 110

Gly Lys Gly Thr His Leu Ser Leu Phe Phe Val Ile Met Arg Gly Glu
            115                 120                 125

Tyr Asp Ala Leu Leu Pro Trp Pro Phe Lys Gln Lys Val Thr Leu Met
130                 135                 140

Leu Met Asp Gln Gly Ser Ser Arg Arg His Leu Gly Asp Ala Phe Lys
145                 150                 155                 160

Pro Asp Pro Asn Ser Ser Ser Phe Lys Lys Pro Thr Gly Glu Met Asn
                165                 170                 175

Ile Ala Ser Gly Cys Pro Val Phe Val Ala Gln Thr Val Leu Glu Asn
            180                 185                 190

Gly Thr Tyr Ile Lys Asp Asp Thr Ile Phe Ile Lys Val Ile Val Asp
            195                 200                 205
```

-continued

```
Thr Ser Asp Leu Pro Asp Pro Ala Ser Ala Ser Ser Lys Arg Ser Met
    210                 215                 220

Asn Asp Pro Tyr
225
```